(12) United States Patent
Chui et al.

(10) Patent No.: US 6,607,899 B2
(45) Date of Patent: Aug. 19, 2003

(54) AMPLIFICATION-BASED CLONING METHOD

(76) Inventors: Clarissa J. Chui, 1 DNA Way, South San Francisco, CA (US) 94080; J. Christopher Grimaldi, 1 DNA Way, South San Francisco, CA (US) 94080; Sean Milton, 1 DNA Way, South San Francisco, CA (US) 94080; Minhong Yan, 1 DNA Way, South San Francisco, CA (US) 94080; Sothy Yi, 1 DNA Way, South San Francisco, CA (US) 94080

( * ) Notice: Subject to any disclaimer, the term of this patent is extended or adjusted under 35 U.S.C. 154(b) by 33 days.

(21) Appl. No.: 10/119,466

(22) Filed: Apr. 9, 2002

(65) Prior Publication Data

US 2002/0168674 A1 Nov. 14, 2002

Related U.S. Application Data

(63) Continuation of application No. 09/480,782, filed on Jan. 10, 2000.
(60) Provisional application No. 60/128,849, filed on Apr. 12, 1999.

(51) Int. Cl.$^7$ .............................. C12P 19/34; C12Q 1/68; C12N 15/09
(52) U.S. Cl. ................... 435/91.2; 435/320.1; 435/455; 435/6
(58) Field of Search ........................ 435/91.2, 6, 320.1, 435/455

(56) References Cited

U.S. PATENT DOCUMENTS

| | | | |
|---|---|---|---|
| 5,314,809 A | | 5/1994 | Erlich et al. |
| 5,500,356 A | | 3/1996 | Li et al. |
| 5,514,568 A | | 5/1996 | Stemmer |
| 5,789,166 A | * | 8/1998 | Bauer et al. .................. 435/6 |
| 6,004,783 A | | 12/1999 | Ausubel et al. |

OTHER PUBLICATIONS

Zilberberg et al. (Analytical Biochemistry 209, 203–205 (1995)).*

Benkel and Fong, "Long range–inverse PCR (LR–IPCR): extending the useful range of inverse PCR" *Genetic Analysis: Biomolecular Engineering* 13(5):123–127 (Nov. 1996).

Chen et al., "Identification of Two hERR2–related Novel Nuclear Receptors Utilizing Bioinformatics and Inverse PCR" *Gene* 228:101–109 (1999).

Fisher and Pei, "Modification of a PCR–based site–directed mutagenesis method" *Biotechniques* 23(4):570–571, 574 (Oct. 1997).

Lelias et al., "Human Universal cDNA Library Array I" *Strategies* 11:29–32 (1998).

Li and Wilkinson, "Site–directed mutagenesis: a two–step method using PCR and DpnI" *Biotechniques* 23(4):588, 590 (Oct. 1997).

Ochman et al., "Amplification of flanking sequences by inverse PCR" *PCR Protocols: A Guide to Methods and Applications*, San Diego:Academic Press pp. 219–227 (1990).

Ochman et al., "Genetic applications of an inverse PCR reaction" *Genetics* 120:621–623 (1988).

Stemmer and Morris, "Enzymatic inverse PCR: a restriction site independent, single–fragment method for high–efficiency, site–directed mutagenesis" *Biotechniques* 13(2):214–220 (Aug. 1992).

*Stratagene Catalog* pps. 176 (1995).

Weiner et al., "Site–directed mutagenesis of double–stranded DNA by the polymerase chain reaction" *Gene* 151(1–2):119–123 (Dec. 30, 1994).

Zilberberg et al. *Analytical Biochemistry* 209:203–205 (1993).

* cited by examiner

*Primary Examiner*—Jeffrey Fredman
*Assistant Examiner*—Juliet C. Einsmann

(57) ABSTRACT

The invention provides a method for isolating a gene of interest from a cDNA library, which involves the use of an amplification step to amplify the gene of interest and an enrichment step to remove the template plasmids.

22 Claims, 5 Drawing Sheets

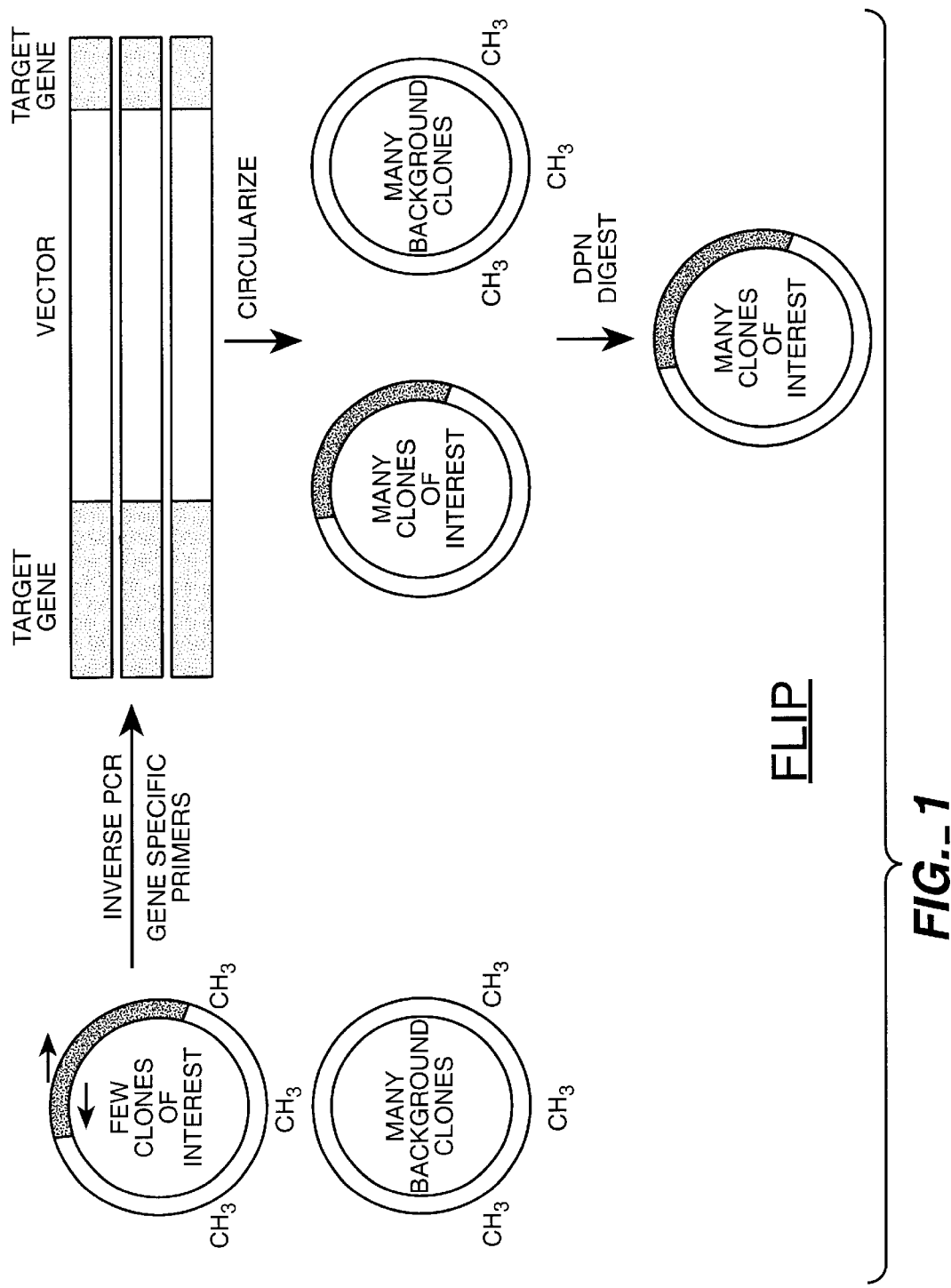
FIG._1

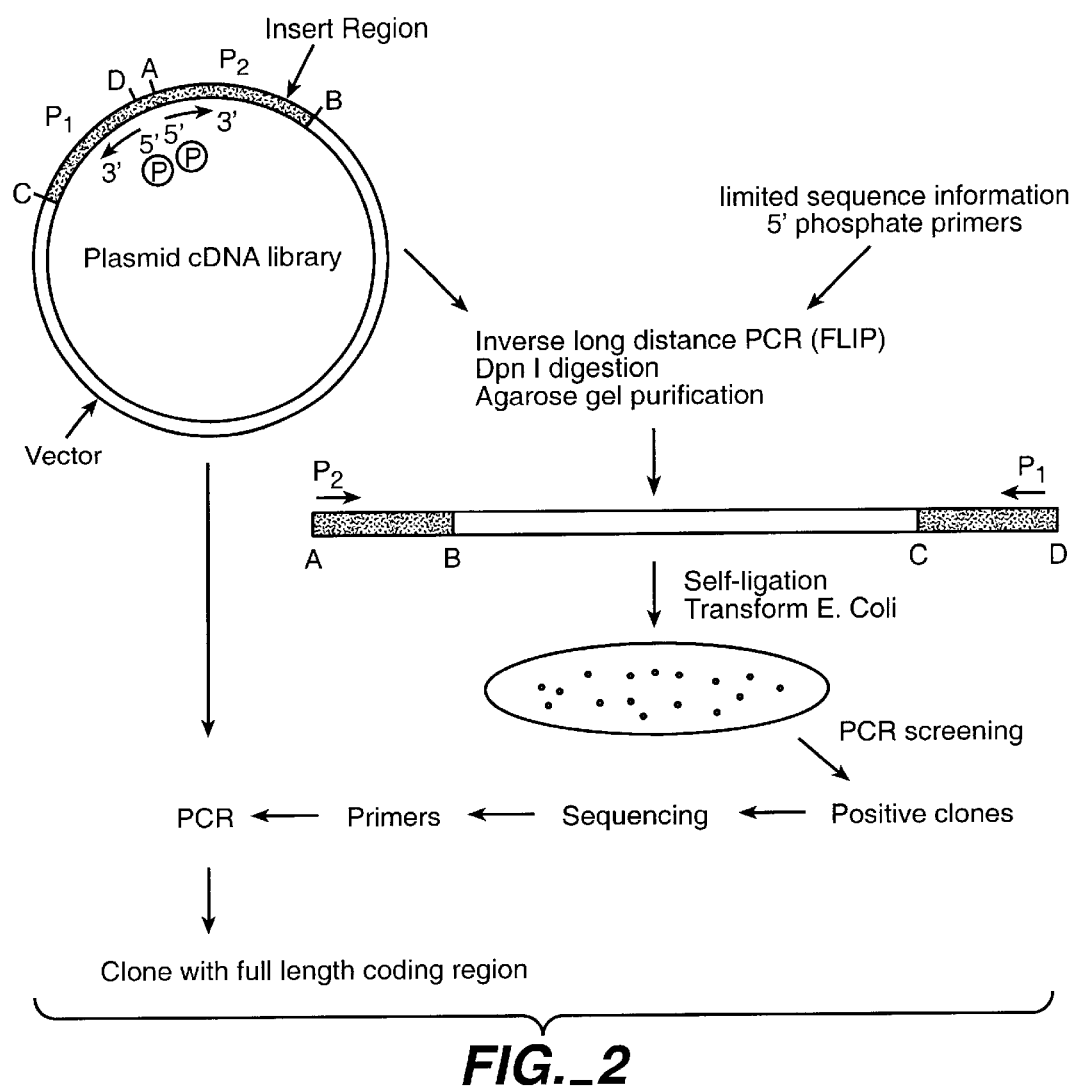
FIG._2

```
  1 GGAGGGGGCT GGGTGAGATG TGTGCTCTGC GCTGAGGTGG ATTTGTACCG GAGTCCCATT TGGGAGCAAG AGCCATCTAC TCGTCCGTTA CCGGCCTTCC
    CCTCCCCCGA CCCACTCTAC ACACGAGACG CGACTCCACC TAAACATGGC CTCAGGGTAA ACCCTCGTTC TCGGTAGATG AGCAGGCAAT GGCCGGAAGG
        ^forward primer 509-1                                                                ^left primer 1: 509-P5

101 CACCATGGAT TGCCAAGAAA ATGAGTACTG GGACCAATGG GGACGGTGTG TCACCTGCCA ACGGTGTGGT CCTGGACAGG AGCTATCCAA GGATTGTGGT
    GTGGTACCTA ACGGTTCTTT TACTCATGAC CCTGGTTACC CCTGCCACAC AGTGGACGGT TGCCACACCA GGACCTGTCC TCGATAGGTT CCTAACACCA
             ^right primer 2: 509-P6

201 TATGGAGAGG GTGGAGATGC CTACTGCACA GCCTGCCCTC CTCGCAGGTA CAAAAGCAGC TGGGGCCACC ACAAATGTCA GAGTTGCATC AC
    ATACCCTCTCC CACCTCTACG GATGACGTGT CGGACGGGAG GAGCGTCCAT GTTTTCGTCG ACCCCGGTGG TGTTTACAGT CTCAACGTAG TG
                                              ^reverse primer 509-4AS
```

FIG._3

```
  1 ACCATGGATT GCCAAGAAAA TGAGTACTGG GACCAATGGG GACGGTGTGT CACCTGCCAA CGGTGTGGTC CTGGACAGGA GCTATCCAAG GATTGTGGTT
    TGGTACCTAA CGGTTCTTTT ACTCATGACC CTGGTTACCC CTGCCACACA GTGGACGGTT GCCACACCAG GACCTGTCCT CGATAGGTTC CTAACACCAA
                           ^ORF starts here
                                                 ^cysteine-rich repeat 1
101 ATGGAGAGGG TGGAGATGCC TACTGCACAG CCTGCCCTCC TCGCAGGTAC AAAAGCAGCT GGGGCCACCA CAGATGTCAG AGTTGCATCA CCTGTGCTGT
    TACCTCTCCC ACCTCTACGG ATGACGTGTC GGACGGGAGG AGCGTCCATG TTTTCGTCGA CCCCGGTGGT GTCTACAGTC TCAACGTAGT GGACACGACA
                                                 ^cysteine-rich repeat 2
201 CATCAATCGT GTTCAGAAGG TCAACTGCAC AGTACCTCT AATGCTGTCT GTGGGGACTG TTTGCCCAGG TTCTACCGAA AGACACGCAT TGGAGGCCTG
    GTAGTTAGCA CAAGTCTTCC AGTTGACGTG TCGATGGAGA TTACGACAGA CACCCCTGAC AAACGGGTCC AAGATGGCTT TCTGTGCGTA ACCTCCGGAC
                                                              ^cysteine-rich repeat 3
301 CAGGACCAAG AGTGCATCCC GTGCACGAAG CAGACCCCCA CCTCTGAGGT TTCCAGTTGA GCTTAGTGGA GGCAGATGCA CCCACAGTGC
    GTCCTGGTTC TCACGTAGGG CACGTGCTTC GTCTGGGGGT GGAGACTCCA AGTTACACGG AAGGTCAACT CGAATCACCT CCGTCTACGT GGGTGTCACG
401 CCCCTCAGGA GGCCACACTT GTTGCACTGG TGAGCAGCCT GCTAGTGGTG TTTACCCTGG CCTTCCTGGG GCTCTTCTTC CTCTACTGCA AGCAGTTCTT
    GGGGAGTCCT CCGGTGTGAA CAACGTGACC ACTCGTCGGA CGATCACCAC AAATGGGACC GGAAGGACCC CGAGAAGAAG GAGATGACGT TCGTCAAGAA
                                                 ^transmembrane domain
501 CAACAGACAT TGCCAGCGTG TTACAGGAGG TTTGCTGCAG CCCAGCCACT ATAAAACAGC AAAGGAGGAA TCTCTCTTCC CCGTGCCACC CAGCAAGGAG
    GTTGTCTGTA ACGGTCGCAC AATGTCCTCC AAACGACGTC GGGTCGGTGA TATTTTGTCG TTTCCTCCTT AGAGAGAAGG GGCACGGTGG GTCGTTCCTC
601 ACCAGTGCTG AGTCCCAAGT GAGTGAGAAC ATCTTTCAGA CCCAGCCACT TAACCCTATC CTCGAGGACG ACTGCAGCTC GACTAGTGGC TTCCCCACAC
    TGGTCACGAC TCAGGGTTCA CTCACTCTTG TAGAAAGTCT GGGTCGGTGA ATTGGGATAG GAGCTCCTGC TGACGTCGAG CTGATCACCG AAGGGGTGTG
701 AGGAGTCCTT TACCATGGCC TCCTGCACCT CAGAGAGCCA GTCCCACAGC CTCCCACTGG GTCCCACTGG CAGGTGTGAC GGTAGCTTAC GTGTCTCGAC
    TCCTCAGGAA ATGGTACCGG AGGACGTGGA GTCTCTCGGT CAGGGTGACC GAGGGTGACC CAGGGTGACC GGTAGCTTAC GTGTCTCGAC CTGGACGTTT TCAAAAGGTC
801 CTCTGCCTCC TATACTGGAG CTGAGACCTT GGGGGGAAAC ACAGTCGAAA GCACTGGAGA CAGGCTGGAG CTCAATGTGC CCTTTGAAGT TCCCAGCCCT
    GAGACGGAGG ATATGACCTC GACTCTGGAA CCCCCCTTTG TGTCAGCTTT CGTGACCTCT GTCCGACCTC GAGTTACACG GGAAACTTCA AGGGTCGGGA
901 TAAGC
    ATTCG
```

FIG._4

```
          10         20         30         40         50
          |          |          |          |          |
MDCQENEYWDQWGRCVTCQRCGPGQELSKDCGYGEGGDAYCTACPPRRYK 60         70         80         90        100
          |          |          |          |          |
SSWGHHRCQSCITCAVINRVQKVNCTATSNAVCGDCLPRFYRKTRIGGLQ 110        120        130        140        150
          |          |          |          |          |
DQECIPCTKQTPTSEVQCAFQLSLVEADAPTVPPQEATLVALVSSLLVVF 160        170        180        190        200
          |          |          |          |          |
TLAFLGLFFLYCKQFFNRHCQRVTGGLLQFEADKTAKEESLFPVPPSKET 210        220        230        240        250
          |          |          |          |          |
SAESQVSENIFQTQPLNPILEDDCSSTSGFPTQESFTMASCTSESHSHWV 260        270        280        290
          |          |          |          |
HSPIECTELDLQKFSSSASYTGAETLGGNTVESTGDRLELNVPFEVPSP
```

FIG._5

SEQUENCE LISTING

<160> NUMBER OF SEQ ID NOS: 12

<210> SEQ ID NO 1
<211> LENGTH: 33
<212> TYPE: DNA
<213> ORGANISM: Artificial sequence
<220> FEATURE:
<223> OTHER INFORMATION: Sequence source:  PCR primer, 33 bases

<400> SEQUENCE: 1
gctatcctaa agggttgttc ttcttcagag cat                               33

<210> SEQ ID NO 2
<211> LENGTH: 29
<212> TYPE: DNA
<213> ORGANISM: Artificial sequence
<220> FEATURE:
<223> OTHER INFORMATION: Sequence source:  PCR primer, 29 bases

<400> SEQUENCE: 2
cactgcaaca tcatgaccaa agacaaaga                                    29

<210> SEQ ID NO 3
<211> LENGTH: 27
<212> TYPE: DNA
<213> ORGANISM: Artificial sequence
<220> FEATURE:
<223> OTHER INFORMATION: Sequence source:  Toll 6-specific probe, 27
      bases

<400> SEQUENCE: 3
gttagcctgc cagttagaga cagccca                                      27

<210> SEQ ID NO 4
<211> LENGTH: 292
<212> TYPE: DNA
<213> ORGANISM: Homo sapiens
<220> FEATURE:
<221> NAME/KEY: Homo sapiens
<222> LOCATION: 1-292
<223> OTHER INFORMATION:

<400> SEQUENCE: 4 ggaggggggct gggtgagatg tgtgctctgc gctgaggtgg atttgtaccg             50
gagtcccatt tgggagcaag agccatctac tcgtccgtta ccggccttcc             100
caccatggat tgccaagaaa atgagtactg ggaccaatgg ggacggtgtg             150
tcacctgcca acggtgtggt cctggacagg agctatccaa ggattgtggt             200
tatggagagg gtggagatgc ctactgcaca gcctgccctc ctcgcaggta             250
caaaagcagc tggggccacc acaaatgtca gagttgcatc ac                     292

<210> SEQ ID NO 5
<211> LENGTH: 21
<212> TYPE: DNA
<213> ORGANISM: Artificial sequence
<220> FEATURE:
<223> OTHER INFORMATION: Sequence source:  PCR primer, 21 bases

<400> SEQUENCE: 5 gaggggctg ggtgagatgt g                                              21

<210> SEQ ID NO 6

```
<211> LENGTH: 22
<212> TYPE: DNA
<213> ORGANISM: Artificial sequence
<220> FEATURE:
<223> OTHER INFORMATION: Sequence source:  PCR primer, 22 bases

<400> SEQUENCE: 6
tgcttttgta cctgcgagga gg                                        22

<210> SEQ ID NO 7
<211> LENGTH: 22
<212> TYPE: DNA
<213> ORGANISM: Artificial sequence
<220> FEATURE:
<223> OTHER INFORMATION: Sequence Source:  PCR primer, 22 bases

<400> SEQUENCE: 7
catggtggga aggccggtaa cg                                        22

<210> SEQ ID NO 8
<211> LENGTH: 28
<212> TYPE: DNA
<213> ORGANISM: Artificial sequence
<220> FEATURE:
<223> OTHER INFORMATION: Sequence source:  PCR primer, 28 bases

<400> SEQUENCE: 8
gattgccaag aaaatgagta ctgggacc                                  28

<210> SEQ ID NO 9
<211> LENGTH: 35
<212> TYPE: DNA
<213> ORGANISM: Artificial sequence
<220> FEATURE:
<223> OTHER INFORMATION: Sequence source:  PCR primer, 35 bases

<400> SEQUENCE: 9
ggaggatcga taccatggat tgccaagaaa atgag                          35

<210> SEQ ID NO 10
<211> LENGTH: 41
<212> TYPE: DNA
<213> ORGANISM: Artificial sequence
<220> FEATURE:
<223> OTHER INFORMATION: Sequence source:  PCR primer, 41 bases

<400> SEQUENCE: 10
ggaggagcgg ccgcttaagg gctgggaact tcaaagggca c                   41

<210> SEQ ID NO 11
<211> LENGTH: 905
<212> TYPE: DNA
<213> ORGANISM: Homo sapiens
<220> FEATURE:
<221> NAME/KEY: Homo sapiens
<222> LOCATION: 1-905
<223> OTHER INFORMATION: Sequence source:  ORF position 4 - 903 bp

<400> SEQUENCE: 11
accatggatt gccaagaaaa tgagtactgg gaccaatggg gacggtgtgt           50
cacctgccaa cggtgtggtc ctggacagga gctatccaag gattgtggtt          100
atggagaggg tggagatgcc tactgcacag cctgccctcc tcgcaggtac          150
aaaagcagct ggggccacca cagatgtcag agttgcatca cctgtgctgt          200
catcaatcgt gttcagaagg tcaactgcac agctacctct aatgctgtct          250
```

```
gtggggactg tttgcccagg ttctaccgaa agacacgcat tggaggcctg        300
caggaccaag agtgcatccc gtgcacgaag cagaccccca cctctgaggt        350
tcaatgtgcc ttccagttga gcttagtgga ggcagatgca cccacagtgc        400
cccctcagga ggccacactt gttgcactgg tgagcagcct gctagtggtg        450
tttaccctgg ccttcctggg gctcttcttc ctctactgca agcagttctt        500
caacagacat tgccagcgtg ttacaggagg tttgctgcag tttgaggctg        550
ataaaacagc aaaggaggaa tctctcttcc ccgtgccacc cagcaaggag        600
accagtgctg agtcccaagt gagtgagaac atctttcaga cccagccact        650
taaccctatc ctcgaggacg actgcagctc gactagtgga ttccccacac        700
aggagtcctt taccatggcc tcctgcacct cagagagcca ctcccactgg        750
gtccacagcc ccatcgaatg cacagagctg gacctgcaaa agttttccag        800
ctctgcctcc tatactggag ctgagacctt gggggaaac acagtcgaaa         850 gcactggaga caggctggag ctcaatgtgc cctttgaagt tcccagccct        900
taagc                                                         905
```

```
<210> SEQ ID NO 12
<211> LENGTH: 299
<212> TYPE: PRT
<213> ORGANISM: Homo sapiens
<220> FEATURE:
<221> NAME/KEY: Homo sapiens
<222> LOCATION: 1-299
<223> OTHER INFORMATION:

<400> SEQUENCE: 12
```

```
Met Asp Cys Gln Glu Asn Glu Tyr Trp Asp Gln Trp Gly Arg Cys
 1               5                  10                  15

Val Thr Cys Gln Arg Cys Gly Pro Gly Gln Glu Leu Ser Lys Asp
                20                  25                  30

Cys Gly Tyr Gly Glu Gly Gly Asp Ala Tyr Cys Thr Ala Cys Pro
                35                  40                  45

Pro Arg Arg Tyr Lys Ser Ser Trp Gly His His Arg Cys Gln Ser
                50                  55                  60

Cys Ile Thr Cys Ala Val Ile Asn Arg Val Gln Lys Val Asn Cys
                65                  70                  75

Thr Ala Thr Ser Asn Ala Val Cys Gly Asp Cys Leu Pro Arg Phe
                80                  85                  90

Tyr Arg Lys Thr Arg Ile Gly Gly Leu Gln Asp Gln Glu Cys Ile
                95                 100                 105

Pro Cys Thr Lys Gln Thr Pro Thr Ser Glu Val Gln Cys Ala Phe
               110                 115                 120

Gln Leu Ser Leu Val Glu Ala Asp Ala Pro Thr Val Pro Pro Gln
               125                 130                 135

Glu Ala Thr Leu Val Ala Leu Val Ser Ser Leu Leu Val Val Phe
               140                 145                 150

Thr Leu Ala Phe Leu Gly Leu Phe Phe Leu Tyr Cys Lys Gln Phe
               155                 160                 165

Phe Asn Arg His Cys Gln Arg Val Thr Gly Gly Leu Leu Gln Phe
               170                 175                 180

Glu Ala Asp Lys Thr Ala Lys Glu Glu Ser Leu Phe Pro Val Pro
               185                 190                 195
```

-continued

```
Pro Ser Lys Glu Thr Ser Ala Glu Ser Gln Val Ser Glu Asn Ile
                200             205             210

Phe Gln Thr Gln Pro Leu Asn Pro Ile Leu Glu Asp Asp Cys Ser
                215             220             225

Ser Thr Ser Gly Phe Pro Thr Gln Glu Ser Phe Thr Met Ala Ser
                230             235             240

Cys Thr Ser Glu Ser His Ser His Trp Val His Ser Pro Ile Glu
                245             250             255

Cys Thr Glu Leu Asp Leu Gln Lys Phe Ser Ser Ser Ala Ser Tyr
                260             265             270

Thr Gly Ala Glu Thr Leu Gly Gly Asn Thr Val Glu Ser Thr Gly
                275             280             285

Asp Arg Leu Glu Leu Asn Val Pro Phe Glu Val Pro Ser Pro
                290             295             299
```

AMPLIFICATION-BASED CLONING METHOD

This is a continuation application filed under 37 CFR 1.53(b) of application Ser. No. 09/480,782 filed Jan. 10, 2000, which claims priority under Section 119(e) to provisional application No. 60/128,849 filed on Apr. 12, 1999, which applications are incorporated herein in their entirety by reference.

FIELD OF THE INVENTION

The invention concerns a method for the enrichment and isolation of genes of interest from recombinant DNA libraries.

BACKGROUND OF THE INVENTION

Recombinant DNA (including cDNA and genomic) libraries consist of a large number of recombinant DNA clones, each containing a different segment of foreign DNA. In order to ensure that a recombinant cDNA library contains at least one copy of each mRNA in the cell, it generally needs to include between about 500,000 and 1,000,000 independent cDNA clones. *Current Protocols in Molecular Biology*, Ausubel et al., editors, Greene Publishing Associates and Wiley-Interscience, N.Y., 1991, vol. 1, Unit 5.8.1. Similarly, a genomic library with a base of about 700,000 clones is required to obtain a complete library of mammalian DNA. Ausubel et al., supra, Unit 5.7.1. While the frequency of different genes in any particular library varies, most genes will be present at a frequency of about 1 part in $10^3$ to $10^6$. A particularly rare mRNA will be represented by a single clone out of $10^6$ clones, while the majority of the genes will be present at a frequency of 1 in $10^4$ to $10^5$ clones.

The identification and isolation of any desired recombinant DNA clone from among such a daunting number of total clones is not an easy task. Over the past 25 years, several cloning methods have been developed. In most cases, desired clones are identified by screening DNA libraries with nucleic acid probes, ligands or antibodies. Usually, libraries are introduced into host cells, plated out, colonies transferred to nitrocellulose filters, and hybridized to $^{32}$P-labeled probes or bound to antibodies. Such filter hybridization methods (see Sambrook et al., 1989, infra) do not involve an enrichment step. In order to clone a particular gene, sometimes as many as one million clones must be screened. Subtractive hybridization techniques have also been used to isolate target DNA. In this technique, the cDNA molecules created from a first population of cells is hybridized to cDNA or RNA of a second population of cells in order to "subtract out" those cDNA molecules that are complementary to nucleic acid molecules present in the second population that reflect nucleic acid molecules present in both populations, therefore leaving only molecules unique to the population of interest.

Inverse polymerase chain reaction (IPCR) has been described, see Ochman et al. Genetic applications of an inverse PCR reaction, *Genetics* 120: 621 (1988)). In IPCR, the primers are oriented in the reverse direction of the usual orientation in conventional PCR, i.e., the two primers extend away from each other. Inverse PCR was originally used to amplify uncharacterized sequences immediately flanking transposable elements. Inverse PCR has been used to isolate a target gene; however, there is no selection or enrichment for the target gene in conventional inverse PCR protocols, resulting in a high background of colonies.

Li et al. in U.S. Pat. Nos. 5,500,356, and 5,789,166, describe a method of isolating a desired target nucleic acid from a nucleic acid library, that involves the use of biotinylated probes and enzymatic repair-cleavage to eliminate the parental template nucleic acid of the library. This method requires a single stranded nucleic acid library (M13 phagemid library). If the library consists of double stranded plasmids, single strands have to be prepared initially. A biotinylated oligonucleotide probe is hybridized to a target sequence within the single-stranded molecules. This hybridized complex is then captured on avidin-coated beads and the library recovered from the beads by denaturation of the hybridized molecules. This selection eliminates undesired single-stranded phagemid DNA. This method of cloning does not involve amplification of the target gene before the selection step. The recovered single-stranded DNA is converted to ds DNA in the presence of dNTPs (but not dUTP) and then the mixture digested with the enzyme HhaI that digests away residual ss DNA that contain dUTP. Transformation and isolation of the desired molecule follows.

PCR based site-directed mutagenesis has been used to create a desired mutation such as a point mutation, deletion or insertion. In the site-directed mutagenesis method of Bauer et al., U.S. Pat. No. 5,789,166, the starting DNA template for the PCR amplification is typically a homogeneous population of plasmids all containing the one insert of interest that is to be mutated. Both oligonucleotide primers for such a PCR reaction are mutagenic primers which must contain the desired mutation; for point mutations, these primers are designed to contain at least one mismatched base relative to the template which upon primer extension will result in the desired mutation of the target gene. For the point mutations, the primers are overlapping, i.e., they need to anneal to the same sequence on opposite strands of the plasmid. For deletion mutagenesis, the primers are designed such that there is a gap between the 5' ends of the primer pair. Thus, the product of the primer extension has a gap in the sequence of the target gene corresponding to the sequence to be deleted. Mutated plasmids containing the desired mutation are selected for and transformed into competent bacteria.

From the above discussion, it is apparent that there is a need for a cloning method that is versatile, easier to perform and less laborious, that can provide higher throughput, and is economical. The present invention overcomes the limitations of conventional cloning methods and provides additional advantages that will be apparent from the detailed description below.

SUMMARY OF THE INVENTION

The invention provides a method of amplifying and isolating a nucleic acid molecule of interest from a mixture of nucleic acid molecules, comprising:

(i) providing a recombinant nucleic acid library with a heterogeneous population of methylated, circular nucleic acid molecules as template molecules;

(ii) annealing a first and a second primer to complementary strands of the circular nucleic acid molecule, to produce an annealed mixture, wherein
the two primers in the 5' to 3' direction, extend in opposite directions relative to each other during polymerase chain reaction;
the 5' ends of the two primers are adjacent to each other; and
wherein each primer is identical in sequence to its corresponding sequence in the nucleic acid molecule of interest;

(iii) subjecting the annealed mixture to polymerase chain reaction, thereby producing an amplified mixture containing linear amplicons;

(iv) digesting the amplified mixture with an enzyme that selectively cleaves methylated DNA, thereby eliminating the template molecules and enriching the nucleic acid molecule of interest; and (v) isolating the nucleic acid molecule of interest.

In one embodiment, the first and second primers are provided phosphorylated on their 5' ends. In this embodiment, the method will comprise a ligation step after the PCR step but prior to the digesting step, to ligate the linear amplicons to produce circular replicons. Alternatively, after the digestion step, amplicons larger than the size of the cloning vector of the nucleic acid library are isolated such as by gel purification, and the isolated amplicons ligated.

In a preferred embodiment, the enzyme used to digest the amplified mixture is a restriction endonuclease. In a specific embodiment, the restriction endonuclease is Dpn I.

Multiple recombinant nucleic acid libraries can be mixed into a single reaction mix for polymerase chain reaction. In addition, multiple nucleic acid molecules of interest can be cloned simultaneously by applying aliquots of a solution of the mixed libraries to wells of a 96-well microtiter plate and performing the polymerase chain reaction on the microtiter plate.

In one embodiment, the nucleic acid library is a double-stranded DNA library wherein the DNA is methylated. Preferred DNA libraries are human cDNA or human genomic DNA libraries. Preferably, the nucleic acid molecule of interest is represented in the library at a frequency of greater than $5 \times 10^5$, even more preferably, at a frequency of equal to or greater than $1 \times 10^6$.

The method of the above embodiments further comprises the step of transforming the circular replicons into a suitable host cell after the digesting step, to generate clones. In one embodiment, the host cell is a competent bacterial host cell. The clones are then screened to identify the clone containing the nucleic acid molecule of interest. In an alternative embodiment, the screening step is omitted and the clones are directly sequenced. Sequencing is performed on nucleic acid isolated from the clones. Nucleic acid from multiple clones can be pooled for the sequencing step.

The invention provides a method of amplifying and isolating a nucleic acid molecule of interest from a recombinant nucleic acid library, comprising:

(i) providing a recombinant nucleic acid library with a heterogeneous population of methylated, circular nucleic acid molecules as template molecules;

(ii) annealing a first and a second primer to complementary strands of the circular nucleic acid molecule, to produce an annealed mixture, wherein
the two primers extend in opposite directions relative to each other during polymerase chain reaction;
the 5' ends of the two primers are phosphorylated and adjacent to each other; and
wherein each primer is identical in sequence to its corresponding sequence in the nucleic acid molecule of interest;

(iii) subjecting the annealed mixture to polymerase chain reaction, thereby producing an amplified mixture containing amplicons;

(iv) ligating the amplicons in a ligation mix to produce circular replicons;

(v) subjecting the ligation mix after ligation to digestion with an enzyme that selectively cleaves methylated nucleic acid, thereby eliminating the template molecules and enriching the nucleic acid molecule of interest;

(vi) transforming the replicons into a suitable host cell to generate transformed clones; and (vii) isolating the nucleic acid molecule of interest.

In one embodiment of the preceding method, a screening step is provided to screen the transformed clones to identify the clone containing the nucleic acid molecule of interest.

In any of the above embodiments, greater than 50 cDNA libraries can be provided in a single mix for polymerase chain reaction.

BRIEF DESCRIPTION OF THE FIGURES

FIG. 1 is a flow chart illustrating the FLIP cloning method up to the restriction digestion (with Dpn I in this case) selection step, as described in detail in Example 1. The shaded boxes flanking the vector sequence represent the target gene sequences.

FIG. 2 is a flow chart showing one alternative embodiment to the above FLIP procedure, as performed in Example 2.

FIG. 3 shows the nucleotide sequence of Incyte clone 509 1511H. (SEQ ID No:4), as used in Example 2.

FIG. 4 shows a nucleotide sequence (SEQ ID NO:11) of a native sequence DNA98853 polypeptide cDNA (nucleotides 1–903). Also presented is the position of three cysteine-rich repeats encoded by nucleotides 10–126, 133–252 and 259–357 as underlined. The putative transmembrane domain of the protein is encoded by nucleotides 409–474 in the figure. See Example 2.

FIG. 5 shows the amino acid sequence (SEQ ID NO:12) derived from nucleotides 4–900 of the nucleotide sequence shown in FIG. 4. A potential transmembrane domain exists between and including amino acids 137 to 158 in the figure. See Example 2.

DETAILED DESCRIPTION OF THE INVENTION

A. Definitions

An "amplicon" is a product of a polymerase chain reaction extended from the two primers of the primer pair used in the reaction.

A "replicon" is a nucleic acid molecule capable of being replicated in a suitable host cell. Generally, a replicon will have an origin of replication for replication in a compatible host cell.

The nucleic acid molecule of interest is isolated from a mixture or library of cloned molecules. The clones comprises DNA or RNA or mixed polymer molecules that may be either single-stranded or double-stranded. Typically, the library of clones will comprise plasmids or other vectors (such as viral vectors) prepared using recombinant DNA methods, i.e., recombinant nucleic acid library, to contain a fragment of DNA or RNA derived from a nucleic acid source such as cells of a cell line, or primary cells or a tissue. The cells may be prokaryotic or eukaryotic cells (including animals, humans, yeast and higher plants). The nucleic acid library will contain a heterogeneous population of clones. In preferred embodiments, the nucleic acid molecule of interest is a gene comprising an open reading frame and may further include 5' and/or 3' untranslated regions (UT). Where the examples use the term "target gene" or "gene of interest", it will be understood they encompass "nucleic acid molecule of interest".

Unless otherwise indicated, the term "DNA" is used to refer collectively to genomic DNA and cDNA, prepared from any source, including bacteria, plant cells, and mammalian cells, preferably cells of high primates, such as monkeys or humans, most preferably humans.

The phrase "recombinant DNA library" is used to refer collectively to genomic and cDNA libraries. Preferably, a "recombinant DNA library" contains a substantially complete representation of all genomic or cDNA sequences from a particular cell or tissue source.

For genomic DNA libraries, the "frequency" of any given gene is the ratio of a particular gene fragment of a given length to the total number of base pairs (bp) present in the genome. For example, if the genome consists of $3 \times 10^9$ base pairs, a particular 3000-bp gene of interest will be present at a frequency of 1 part in $10^6$. The "frequency" of a particular cDNA within a cDNA library is expressed by the ratio of its mRNA to the total poly(A) containing RNA. This ratio is usually unaffected by the process of copying the mRNA into cDNA.

The technique of "polymerase chain reaction," or "PCR," as used herein generally refers to a procedure wherein minute amounts of a specific piece of nucleic acid, RNA and/or DNA, are amplified as described in U.S. Pat. No. 4,683,195 issued Jul. 28, 1987. Generally, some sequence information from the region of interest or beyond needs to be available, such that oligonucleotide primers can be designed; these primers will be identical or similar in sequence to opposite strands on the template to be amplified. Generally, the PCR method involves repeated cycles of primer extension synthesis, using two primers capable of hybridizing preferentially to a template nucleic acid comprising the nucleotide sequence to be amplified. If the template nucleic acid is DNA, the DNA to be amplified is denatured by heating the sample. In the presence of DNA polymerase and excess deoxynucleotide triphosphates, oligonucleotides that anneal specifically to the target sequence prime new DNA synthesis. PCR produces an "amplified mixture" in which the individual amplicons increase exponentially in amount with respect to the number of cycles of primer extension. PCR can be used to amplify specific RNA sequences, specific DNA sequences from total genomic DNA, and cDNA transcribed from total cellular RNA, bacteriophage or plasmid sequences, etc. See, generally, Mullis et al., *Cold Spring Harbor Symp. Quant. Biol.*, 51:263 (1987); Erlich, ed., *PCR Technology*, (Stockton Press, N.Y., 1989); Wang & Mark, in *PCR Protocols* pp.70–75 (Academic Press, 1990); Scharf, in *PCR Protocols*, pp. 84–98; Kawasaki & Wang, in *PCR Technology*, pp. 89–97 (Stockton Press, 1989).

A "primer" as used herein, is a single-stranded oligonucleotide that can be extended by the covalent addition of nucleotide monomers during the template-dependent polymerization reaction catalyzed by a polymerase. The oligonucleotide primers are generally at least 15 nucleotides in length, preferably between about 25 to about 45 bases, more preferably between about 25 to 35 nucleotides, even more preferably between 20–24 nucleotides.

A pair of oligonucleotide primers is used in the inverse PCR step. The two primers of the pair are "adjacent" to each other in the sense that they do not overlap or have any gap in between. "Adjacent" primers are illustrated in FIG. 3 (see left and right primer). As used herein, forward and reverse when used to describe a primer, refer to the direction in which the 3' end of the primer is pointing relative to the target sequence. As used herein, a "forward" primer will extend downstream towards the 3' end of the gene. A reverse primer extends in the opposite direction of the forward primer during primer extension. As an illustration, assuming a nucleic acid fragment arbitrarily numbered base 1–32 serves as a template for the design of the primer pair, and the left primer from 5' to 3' is identical to the upper strand nucleotides 16 down to 1, then the right primer is identical to the lower strand nucleotides 17–32. In this way, the primers do not have gaps or overlaps over the stretch of template sequence.

Two sequences are "complementary" to one another if they are capable of hybridizing to one another to form a stable anti-parallel, double-stranded nucleic acid structure.

In a "ligation" reaction, the ligase enzyme catalyzes the formation of a phosphodiester bond between juxtaposed 5' phosphate and 3' hydroxyl termini in two nucleic acid fragments. To ligate the nucleic acid fragments together, their ends must be compatible. In some cases, the ends will be directly compatible after endonuclease digestion. However, it may be necessary to first convert the staggered ends commonly produced after endonuclease digestion to blunt ends to make them compatible for ligation. To blunt ends, the DNA is treated in a suitable buffer with Klenow fragment of DNA polymerase I or T4 DNA polymerase in the presence of the four deoxyribonucleotide triphosphates. The DNA is then purified such as by phenol-chloroform extraction and ethanol precipitation. The DNA fragments that are to be ligated together are mixed in solution in about equimolar amounts. The solution will include ligase buffer, and a ligase such as T4 DNA ligase at about 10 units per 0.5 µg of DNA. If the DNA is to be ligated into a vector, the vector is first linearized by digestion with the appropriate restriction endonuclease(s). The linearized fragment is then treated with bacterial alkaline phosphatase, or calf intestinal phosphatase to prevent self-ligation during the ligation step.

The term "enriching" or "enrichment" is used to refer to the increase in the frequency of occurrence of a particular nucleic acid molecule within a recombinant nucleic acid library after application of the enrichment step (also referred to herein as selection) of the present invention, relative to the frequency of the particular nucleic acid molecule within the same recombinant nucleic acid library prior to the application of the enrichment step, e.g. the frequency of occurrence of a particular cDNA within a recombinant cDNA library. Accordingly, the degree of enrichment (fold enrichment) is expressed as the ratio of the frequency of occurrence of a particular cDNA within a recombinant DNA library after application of the enrichment method of the present invention, to the frequency of the particular cDNA or corresponding genomic DNA within the library prior to the application of the enrichment method.

"Transformation" means introducing DNA into a host cell so that the DNA is replicable, either as an extrachromosomal element or chromosomal integrant. Transformation is usually performed by electroporation (Miller et al., *Proc. Natl. Acad. Sci. USA* 85 856-860 (1988)), $CaCl_2$ transfection (Mandel and Higa, *J. Mol. Biol.* 53, 159–162 (1970)), Shigekawa and Dower, *BioTechnique* 6, 742–751 (1988)), DEAE-dextran technique (eukaryotic cells, Lopata et al., *Nucleic Acids Res.* 12, 5707 (1984)), and liposome-mediated transfection (Felgner et al., *Proc. Natl. Acad. Sci. USA* 84, 7413–7417 (1987)). Unless otherwise provided, the method used herein for transformation of *E. coli* is electroporation.

The terms "transformant", "transformed host cell" and "transformed" refer to the introduction of DNA into a cell. The cell is termed a "host cell", and it may be a prokaryotic or a eukaryotic cell. Typical prokaryotic host cells include various strains of *E. coli*. Typical eukaryotic host cells are mammalian, such as Chinese hamster ovary cells or human embryonic kidney 293 cells. The introduced DNA sequence may be from the same species as the host cell or a different species from the host cell, or it may be a hybrid DNA sequence, containing some foreign and some homologous DNA.

The term "plate" is used to refer to petri dishes or 96-well microtiter dishes filled with solid medium used to grow separated bacterial colonies or plaques. The terms "plating" or "plating out" refer to the placement of bacteria or phage on plates so that colonies or plaques are formed.

In the context of the present invention the expressions "cell", "cell line", and "cell culture" are used interchangeably, and all such designations include progeny. It is also understood that all progeny may not be precisely identical in DNA content, due to deliberate or inadvertent mutations. Mutant progeny that have the same function or biological property as screened for in the originally transformed cell are included.

B. Preferred Embodiments

The present invention provides a cloning and selection method called Full Length Inverse PCR ("FLIP"), also referred to herein as inverse long distance PCR because of the ability of this method to isolate long genes. FLIP is a very rapid and high throughput method of isolating an entire clone, vector plus insert, of a specific nucleic acid molecule from any nucleic acid library which was propagated in a host cell that methylates the nucleic acid library. The FLIP cloning method amplifies a target gene or nucleotide sequence and generates a highly purified population of the target gene.

There are several advantages of FLIP over conventional cloning methods. The FLIP method is easy to perform, employing standard molecular biology techniques, PCR, ligation, digestion, and DNA hybridization procedures, that ultimately generates a population of clones representing a single gene. The FLIP method is versatile in applications, provides high throughput, and is economical. FLIP allows the cloning of novel as well as known genes; this is in contrast to T/A cloning and standard PCR cloning which require that the full length gene be known in order to clone it. Library array cloning techniques such as HUCL (Human Universal cDNA Library; Stratagene, catalog #937811 & 937820 for HUCL Array I Membranes) cloning system are expensive and or labor intensive, compared to FLIP, and do not yield to high throughput applications. Using the FLIP method, one can simultaneously amplify and clone as many as 96 or more separate target genes in a single FLIP procedure in a few days. A unique advantage of FLIP is that several cDNA libraries can be mixed together and effectively screened in a single FLIP-IPCR reaction. To date, we have mixed 56 separate cDNA libraries into a single mix and routinely and successfully screen this library mixture to isolate specific genes. This mixture of 56 libraries generates a library with a clonal complexity of several hundred million different cDNA clones. Another advantage is that the FLIP procedure can use double stranded cDNA libraries instead of other methods which require single stranded cDNA libraries. Single stranded libraries are typically less complex, have shorter insert sizes than their double stranded counterparts and are more laborious to produce. Thus far, the length of the nucleic acid molecule able to be cloned using the FLIP methodology is only limited by the size of the DNA molecules of the library itself. FLIP enables amplification of rare genes. While the frequency of different genes in any particular library varies, most genes will be present at a frequency of about 1 part in $10^3$ to $10^6$. A particularly rare mRNA will be represented by a single DNA out of about $5 \times 10^5$ or more clones, while the majority of the genes will be present at a frequency of 1 in $10^4$ to $10^5$ clones. In a preferred embodiment, FLIP uses 5' phosphorylated primers instead of non-phosphorylated primers in the inverse PCR step, which allows the amplicon to self-ligate and generate a circular molecule. Due to the use of 5' phosphorylated primers and the fact that the gene of interest is amplified together with the vector sequences, a single ligation event of the ends of the linear amplicon is sufficient to regenerate a replicon that can then be propagated and amplified further in a host cell. More advantageously, due to the selection step, FLIP will typically amplify the gene of interest to high purity instead of generating a positive clone in a sea of background clones. These and other advantages of the FLIP method will be apparent from the following description of the procedure.

In one embodiment, the FLIP method involves the following steps:

(i) Inverse PCR to amplify the entire plasmid containing the nucleic acid of interest plus vector sequences from a nucleic acid library or mixture of libraries;
(ii) Ligation to circularize the amplicon;
(iii) Enzyme digest to eliminate the parental template plasmids of the library;
(iv) Transformation into host cells to amplify the resultant amplified plasmids;
(v) Screening the transformants to isolate the clone with the target gene; and
(vi) Sequencing to identify the target gene.

It will be understood that certain steps can be performed in a different order and certain steps are optional. For example, although the above order of ligation before enzyme digestion is preferred in the present embodiment of FLIP, the amplicons can be treated with Dpn I before the ligation step. In another embodiment, the screening step after transformation can be omitted. Because FLIP can generate highly purified populations of the target gene, it is possible to directly sequence FLIP reaction products by transforming the plasmids remaining after the restriction digest selection, preparing the plasmid DNA from the total population of transformed bacteria, and sequencing the plasmid DNA directly using gene specific primers. To directly sequence FLIP reaction products, the concentration of the target gene is preferably at least 20% of the total genes in the FLIP reaction product mixture. If the concentration of target gene in the FLIP reaction product is below 20% of total genes, the mixture can still sequenced such as by first PCR-amplifying the target gene using a gene specific primer and a vector primer and then sequencing the amplicon. Sequencing of complex mixtures of FLIP reactions will allow for the rapid determination of novel genes without the need to isolate several purified clones.

In an alternative embodiment, following the inverse PCR step, the PCR mixture is treated with an enzyme, typically a restriction enzyme, to digest away the template plasmids, followed by gel purification of PCR amplified products that are larger than the size of the library cloning vector. The gel purified fragments are then self-ligated and transformed into competent bacterial cells. Colonies are then screened for the target gene and plasmids prepared from the positive clones are sequenced.

The steps of the FLIP method will now be described in more detail.

(i) Inverse PCR Step

The starting material for inverse PCR amplification is methylated, circular nucleic acid the source of which can be one or more nucleic acid libraries. The library can be methylated in vivo or in vitro. The DNA library can be a cDNA or a genomic DNA library. The construction of plasmid, cosmid, and phagemid cDNA libraries, or genomic libraries have been described, see, e.g., Sambrook, J. et al., In: Molecular Cloning, A Laboratory Manual, 2nd Ed., Cold Spring Harbor Laboratory Press, Cold Spring Harbor, N.Y. (1989). Usually, the target gene or sequence of interest is amplified from a cDNA library. The vector into which the DNA fragments of the library are inserted will typically contain an origin of replication to allow it to replicate in the appropriate host cell, and additionally, at least one selectable marker. For example, the vector for replication in *E. coli* may include the Col E1 origin of replication and the ampicillin resistance gene as a selectable marker. A β-galactosidase gene may also be included as an additional selectable marker.

To eliminate the steps of initially screening individual libraries to predetermine which library contains the gene of interest and then selecting that library for amplification, with FLIP, the inverse PCR can be performed on a mixture of cDNA libraries. This saves time and labor. The FLIP method has been successfully used to amplify and isolate target genes from a mixture of 8, 10, 15, and even up to 56 separate cDNA libraries in one mix. There is no apparent limit to the number of libraries that can be screened in a single reaction. For example, 96 different target genes can be screened in a single PCR reaction on a microtiter plate, with each well of the 96 well microtiter plate containing a mixture of 15 libraries. Nucleic acid molecules of interest can be amplified from a single mix containing greater than 40, preferably greater than 50, even more preferably greater than 60 libraries. The 56 cDNA libraries prepared from different tissues and cell lines mixed into a single mix generates a library with a clonal complexity of several hundred million different cDNA clones. Several specific genes have been isolated from the 56-library mix, some of which were not successfully isolated by traditional methods. In FLIP, the entire plasmid containing the target gene and vector sequences are amplified by inverse PCR.

For each target gene or nucleic acid sequence of interest, a pair of synthetic oligonucleotide primers is needed for the IPCR step. The primers are each complementary to opposite strands of a stretch of known sequence of the target gene to be isolated. The known sequence can be any sequence that is an indicator of a potential nucleic acid molecule of interest; it may show homology to a domain or a highly conserved region of a known gene. For genomic DNA, one might look for an exon and identify a fragment to make the primers. The known sequence can be an EST (Expressed Sequence Tag) which is usually about 300–600 bases. For the purposes of FLIP, a short region of known sequence, e.g., about 30 bp, is sufficient. The primers for FLIP inverse PCR are identical in sequence to the corresponding stretch of sequences in the target gene; the primer sequence has no mismatch to the template, unlike mutagenic oligonucleotides that intentionally incorporate a mismatch nucleotide in site-directed mutagenesis protocols. The pair of oligonucleotide primers for the inverse PCR are designed in such a way that the primers are adjacent to each other and the 5' to 3' direction of each primer extends in opposite directions relative to each other. The primers do not overlap and they do not have to be the same length.

The primers added to the IPCR reaction mix do not have to be but are preferably phosphorylated on the 5' ends to enable self-ligation of the linear amplicon to generate a replicon. If the primers are not initially phosphorylated, the 5' ends of the amplicon strands can be phosphorylated with a kinase in vitro before ligation.

The oligonucleotide primers are generally at least 15 nucleotides in length, preferably between about 25 to about 45 bases, more preferably between about 25 to 35 nucleotides, even more preferably between 20–24 nucleotides. The amount of PCR primers used can be varied a lot, by as much as 10-fold. Usually, the primers are used at a final concentration of about 1 μM (See e.g., Molecular Cloning: A Laboratory Manual, J. Sambrook et al., Cold Spring Harbor Laboratory, Cold Spring Harbor, N.Y., 1989, section 14.15). The melting temperature (tm) can be varied. In one embodiment, the primers have a tm of 68–71° C. to optimize specific hybridization to the target sequence. In a preferred embodiment, the primers of each primer pair have a tm of within 1° C. of each other. Other parameters to be taken into account in the design of PCR primers, such as GC content, etc. are as taught in the art. The oligonucleotide primers can be synthesized by known methods and are available custom-designed from commercial sources.

The oligonucleotide primers are annealed to the template strands and first and second DNA strands corresponding to the two DNA strands of the closed circular template DNA are synthesized in an exponential cyclic amplification reaction. The oligonucleotide primers are extended during temperature cycling by using an appropriate polymerase, preferably, a thermostable or thermophilic polymerase. A thermostable polymerase can catalyze nucleotide addition at temperatures of between about 50° C. to about 100° C. Exemplary thermostable polymerases are described in European Patent Application No. 0258017, incorporated herein by reference. Thermophilic DNA polymerases useful in FLIP include Pfu (Pfu Turbo from Stratagene, La Jolla Calif.), the Vent® DNA polymerases (New England BioLabs, Beverly, Mass.), and Platinum Pfx (Life Technologies, Rockville, Md.). Thermostable DNA polymerase with high fidelity (having proofreading properties) and low error rates are preferred. Pfu and Vent polymerases both have an integral 3' to 5' exonuclease proofreading activity that enables the polymerase to correct nucleotide misincorporation errors.

The annealing temperature for annealing of the primers to the template strands can be varied. Preferably, the annealing temperature is between 65°–71° C., preferably 65° C. which provides a high degree of specificity to the gene of interest. Lowering the annealing temperature below 65° C. can reduce specificity.

The number of PCR cycles can be varied; 5, 10, 15, 20 and 23 cycles have been used herein with success. Twenty PCR cycles gives a million fold amplification. For a common gene that is well represented in the cDNA library, 5–10 cycles may be adequate. The number of PCR cycles that will optimize isolation of a possibly rare target gene while maintaining a low PCR-induced mutation rate, is preferred and can be determined by routine methods.

FLIP can be used advantageously to isolate full length known genes. For this, primers for the IPCR step are designed near the 5' ATG start codon. For the screening step, the probe can be designed to the desired 3' end, e.g., at the stop codon. This will favor the isolation of any clones containing the full length sequence between the ATG start and the desired 3' end. FLIP is also useful for amplifying long genes because the DNA polymerases used (e.g., Pfu, Pfx) can polymerize long fragments. Pfu polymerase can polymerize primer extension up to 10 kb, while Pfx can apparently amplify genomic templates up to 12 kb and plasmid templates up to 20 kb. The isolation of the Toll 6 gene which is 4.2 kb in length (open reading frame plus 5' and 3' UT) plus the pRK5D vector of about 5.1 kb adding up to a total amplicon length of about 9.3 kb, illustrates the capabilities of the FLIP cloning method.

(ii) Ligation

The PCR reaction generates a linear, double-stranded DNA amplicon that contains the target gene plus the vector sequences. In a ligation reaction, this linear amplicon is then self-ligated using the 5'-phosphorylated ends of the primer, to regenerate the replicon, able to replicate in the appropriate host cell.

(iii) Enzyme Digest

To select against the parental templates of the library and enrich for the PCR amplified products, the circularized amplicons are then digested with a selection enzyme that the template plasmids are susceptible to. This selection step reduces the background of clones for screening. Typically, the cDNA libraries are propagated in methylation positive bacteria. DNA isolated from almost all *E. coli* strains is dam methylated and is therefore susceptible to digestion by a restriction endonuclease specific for a methylated recognition sequence. Template DNA can also be methylated in vitro. Therefore, at least one restriction enzyme which digests methylated but not unmethylated DNA, can be used to remove the parental template plasmids. Preferably, the restriction enzyme that cleaves methylated DNA is a frequent cutter, i.e., has shorter than a 6-base recognition site, preferably has a 4 base pair recognition site. In one embodiment, the restriction enzyme specific for methylated DNA is Dpn I. Dpn 1 is a 4-base cutter with the recognition sequence 5' G$^m$ATC 3'; it is specific for methylated and hemimethylated DNA. The vector pRK5D has 23 Dpn I sites. Thus, even if the Dpn 1 digestion was only 5% effective, the enzyme would still cut all of the methylated template vectors at least once making the digested vectors incapable of transfoming a bacteria and therefore all transformed bacteria would represent unmethylated, circularized amplicons. Other methylation requiring endonuclease include McrBC (NEB, Beverly, Mass.).

(iv) Transformation

The resultant plasmid replicons after restriction enzyme treatment can be amplified and propagated in suitable host cells, typically competent bacterial cells. Transformation of competent bacteria can be any performed by any method well known in the art and described, e.g., in Sambrook et al., supra. Transformation methods include lipofection, heat shock, electroporation, calcium phosphate co-precipitation, rubidium chloride or polycation (such as DEAE-dextran)-mediated transfection. Competent bacteria for transformation are commercially available and transformation of these cells can be performed following the instructions of the manufacturer. The transformation method that provides optimal transformation frequency is favored. In a preferred embodiment, transformation is by electroporation. Transformation can be performed efficiently in a 96-well format.

(v) Screening

Typically, the FLIP method will amplify the target gene so that it is the major species in the final FLIP reaction product. The transformants, if they are bacteria, are then plated on agar plates, typically under appropriate drug selection depending on the specific selectable marker on the vector. The resultant bacterial colonies are then screened for presence of the target gene by routine methods. Colonies can be screened, e.g., by PCR or colony hybridization.

(vi) From the screening, positive clones are identified and DNA is prepared from the clones for sequencing. Sequencing is performed using routine methods as previously described, e.g., in Sambrook et al. 1989, supra. Sequencing can be preformed on DNA preparations of individual positive clones or pools of clones.

The invention will be more fully understood by reference to the following examples, which are intended to illustrate the invention but not to limit its scope. All literature and patent citations are expressly incorporated by reference.

C. EXAMPLES

Example 1

Isolation of cDNA Clones Encoding Toll 6 Gene

The Toll 6 gene (Genbank Accession# AB020807) has a known sequence of 2760 bp corresponding to its open reading frame (ORF). Using the FLIP methodology in the present experiment, a cDNA clone was isolated which contained the Toll 6 gene that included, in addition to the ORF, the 5' and 3' UT. The total length of the isolated Toll 6 gene was 4.2 kb; the vector pRK5D used was 5.1 kb, thus adding to a total length of 9.3 kb of the DNA molecule amplified by IPCR and isolated.

Toll 6 gene was cloned using FLIP as follows. Two adjacent 5' phosphorylated primers, 128185.snr1 and 128185.snf1, were designed on opposite strands with melting temperatures of 69.3° C. and 69.8° C. respectively. These primers were used in an inverse PCR reaction. The PCR primer sequences were as follows:

128185.snr1 (SEQ ID NO.1) >pGCTATCCTAAAGGGT-TGTTCTTCTTCAGAGCAT and 128185.snf1 (SEQ ID NO.2) >pCACTGCAACATCAT-GACCAAAGACAAAGA.

In a 50 ul reaction, the following reagents were added: 50 ng of a bone marrow cDNA library in the vector pRK5D, which was propagated in a methylation positive bacteria; 50 picomoles of each PCR primer; 10 nmoles of each deoxynucleotide triphosphate, 5 ul of Pfu 10× buffer (Stratagene, La Jolla Calif.), and 1 ul of Pfu Turbo (Stratagene, La Jolla Calif.). The plasmid vector pRK5 (4,661 bp) has been described (EP 307,247 published Mar. 15, 1989); pRK5D (5117 bp) is a derivative of pRK5.

The PCR cycle conditions were one cycle at 94° C. for 3minutes, then 94° C. for 30 seconds, 65° C. for 30 seconds, 72° C. for 13 minutes for 20 cycles. The PCR reaction generated a linear 5' phosphorylated amplicon that contained the Toll 6 cDNA insert plus the pRK5D vector.

Next, 10 ul of the completed PCR reaction was ligated in a 100 ul reaction containing the following other reagents: 10 ul 10× T4 DNA ligase buffer (New England BioLabs, Beverly, Mass.), 4 ul T4 DNA ligase (New England BioLabs, Beverly, Mass.), 76 ul H$_2$O. The ligation was allowed to incubated at ambient temperature for 1 hour on the bench top.

After 1 hour of ligation, 2 ul of the restriction enzyme Dpn1 (New England BioLabs, Beverly, Mass.) was added to the ligation reaction and the digestion was allowed to continue for 1 hour at 37° C. Dpn1 will specifically digest methylated DNA and not unmethylated DNA; therefore, the original bone marrow cDNA library which was used as a template will be digested, leaving only the Toll 6/vector amplicon intact. After the completion of the digestion the sample was cleaned using the QIAquick PCR purification kit (Qiagen, Valencia, Calif.), eluted in 30 ul of elution buffer or H$_2$O and then ethanol precipitated. The pellet was resuspended in 2 ul of H$_2$O and the entire sample was then used to transformed bacteria.

Transformation was done by electroporation into DH 10B electromax competent bacteria (Life Technologies, Rockville, Md.). The transformed bacteria were plated on Luria broth agar plates and colonies allowed to grow overnight at 37° C.

The next day, the colonies were lifted onto a nylon membrane, denatured, renatured and probed with a $^{32}$P-ATP kinase-labeled, Toll 6-specific probe. The sequence of the Toll 6 specific probe was
128185.pI (SEQ ID NO.3) GTTAGCCTGCCAGTTA-GAGACACCCCA.
Positive colonies were sent to sequencing to confirm that the sequence did not contain point mutations introduced by the PCR reaction.

Other known genes of different lengths and base composition were cloned following the procedure as described in this Example. These genes are identified by GenBank Accession Nos. as indicated in Table 1.

Table 2 shows the results of using FLIP to isolate 22 novel (unknown) target genes from a single library, or a mixture of 8 different libraries in a single IPCR reaction mix. The novel genes are identified by DNA#. Table 2 compares the percentage of total plated clones that are positive on probing for the target sequence and the overall success rate of isolating the sought after genes isolated. CFU stand for bacterial colony forming units when plated.

TABLE 1

| Gene | Genbank accession # |
|---|---|
| ADAMS19 | AF134707 |
| Human secreted protein 155 | NM_007126 |
| Peflin | AB026628 |
| HumanTNCB | M18217 |
| PLA-2 | AF058921 |
| OX40 | AR048669 |
| Placental protein | AF051315 |
| FGF16 | AB009391 |
| YLAT-1 | AJ130718 |
| CGI-128 protein | AF151886 |
| CD82 | NM_002231 |
| hPTTG GPI anchored protein | Z48042 |
| Sorting nexon 9 | AF121859 |
| TACC3 | AF093543 |
| Inosine 5' monophosphate | NM_000884 |
| KIAA1O36 | AB028959 |

TABLE 2

| FLIP (8-mix libraries) | | | | FLIP | | |
|---|---|---|---|---|---|---|
| CFU (per ml) | + | % + | Gene # | CFU (per ml) | + | % + |
| 1,670 | 820 | 49 | 01 | 65 | 25 | 38 |
| 1,750 | 1400 | 80 | 02 | 175 | 150 | 86 |
| 900 | 0 | 0 | 03 | 20 | 0 | 0 |
| 25,200 | 18,000 | 71 | 04 | 167 | 110 | 66 |
| 110 | 0 | 0 | 05 | 32 | 0 | 0 |
| 125 | 0 | 0 | 06 | 22 | 0 | 0 |
| 130 | 2 | 1.5 | 07 | 22 | 12 | 55 |
| 300 | 0 | 0 | 08 | 250 | 10 | 4 |
| 4,120 | 0 | 0 | 09 | 2,590 | 0 | 0 |
| 3,000 | 1400 | 47 | 10 | 180 | 150 | 83 |
| 140 | 17 | 12 | 11 | 82 | 0 | 0 |
| 100 | 0 | 0 | 12 | 45 | 0 | 0 |
| 1,160 | 780 | 67 | 13 | 32 | 20 | 63 |
| 5,400 | 302 | 5.6 | 14 | 25 | 0 | 0 |
| 2,000 | 400 | 20 | 15 | 90 | 2 | 2.2 |
| 40 | 0 | 0 | 16 | 7 | 0 | 0 |
| 16,000 | 0 | 0 | 17 | 440 | 0 | 0 |
| 417 | 33 | 7.9 | 18 | 62 | 5 | 8.1 |
| 150 | 15 | 10 | 19 | 122 | 0 | 0 |
| 2,000 | 2 | 0.1 | 20 | 1,930 | 260 | 13 |
| 1,030 | 650 | 63 | 21 | 30 | 2 | 6.6 |
| 1,400 | 30 | 2.1 | 22 | 1,680 | 440 | 26 |

| | FLIP (mixed) | FLIP |
|---|---|---|
| Success Rate | 13/21 (62%) | 11/21 (52%) |
| Average % Positive | 31% (STD 30.11) | 39% (STD 33.11) |

Example 2

Isolation of cDNA Clones Encoding Human DNA98853 Polypeptide

Based upon the DNA sequence of Incyte clone 509 1511H (SEQ ID NO:4) shown in FIG. 3 (from the Incyte Pharmaceuticals LIFESEQ database), oligonucleotides were synthesized to identify by PCR, a cDNA library that contained the sequence of interest. These oligonucleotides were:

```
Forward primer: 5' GAGGGGGCTGGGTGAGATGTG 3'  (509-1)   (SEQ ID NO:5)
Reverse primer: 5' TGCTTTTGTACCTGCGAGGAGG 3' (509-4AS) (SEQ ID NO:6)
```

To isolate the full length coding sequence for DNA98853 polypeptide, the FLIP procedure (also referred to as inverse long distance PCR) was carried out (see FIG. 2). The PCR primers generally ranged from 20 to 30 nucleotides. For inverse long distance PCR, primer pairs were designed in such a way that the 5' to 3' direction of each primer pointed away from each other.

A pair of inverse long distance PCR primers for cloning DNA98853 were synthesized:

```
Primer 1 (left primer):
5' pCATGGTGGGAAGGCCGGTAACG 3'      (509-P5) (SEQ ID NO:7)

Primer 2 (right primer):
5' pGATTGCCAAGAAAATGAGTACTGGGACC 3'  (509-P6) (SEQ ID NO:8)
```

In the inverse long distance PCR reaction, the template is plasmid cDNA library. As a result, the PCR products contain the entire vector sequence in the middle with insert sequences of interest at both ends. After the PCR reaction, the PCR mixture was treated with Dpn I which digests only the template plasmids, followed by agarose gel purification of PCR products of larger than the size of the library cloning vector. Since the primers used in the inverse long distance PCR were also 5'-phosphorylated, the purified products were then self-ligated and transformed into E. coli competent cells. Colonies were screened by PCR using 5' vector primer and proper gene specific primer to identify clones with larger 5' sequence. Plasmids prepared from positive clones were sequenced. If necessary, the process could be repeated to obtain more 5' sequences based on new sequence obtained from the previous round.

The purpose of inverse long distance PCR in this experiment is to obtain the complete sequence of the gene of interest. The clone containing the full length coding region was then obtained by conventional PCR.

The primer pair used to clone the full length coding region of DNA98853 were synthesized:

```
Forward primer:
5' ggaggatcgatACCATGGATTGCCAAGAAAATGAG 3'   (Cla-MD-509) (SEQ ID NO: 9)

Reverse primer:
5' ggaggagcggccgcttaAGGGCTGGGAACTTCAAAGGGCAC (509.TAA.not) (SEQ ID NO:10)
```

For cloning purposes, a Cla I site and a Not I site were included in the forward primer and reverse primer respectively.

To ensure the accuracy of the PCR products, independent PCR reactions were performed and several cloned products were sequenced.

DNA sequencing of the clones isolated as described above gave the full-length DNA sequence for DNA98853 polypeptide (herein designated as DNA93853-1739) (SEQ ID NO:11) and the derived protein sequence for DNA98853 polypeptide (SEQ ID NO:12)

FIG. 1 shows the nucleotide sequence of the ORF of DNA98853. The entire cDNA sequence is much longer and includes 5' and 3' UT (untranslated region). Clone DNA98853-1739 was deposited with the ATCC under the Budapest Treaty, on Apr. 6, 1999 and assigned ATCC Deposit No. ATCC 203906. American Type Culture Collection (ATCC) is located at 10801 University Boulevard, Manassas, Va. 20110-2209. Clone DNA98853 contains a single open reading frame with an apparent translational initiation site at nucleotide positions 4–6 and ending at the stop codon at nucleotide positions 901–903 (FIG. 4). The predicted polypeptide precursor is 299 amino acids long (FIG. 5) (SEQ ID NO:12). The full-length DNA98853 polypeptide protein shown in FIG. 5 has an estimated molecular weight of about 3.3 kilodaltons and a pI of about 4.72. A potential N-glycosylation site exists between amino acids 74 and 77 of the amino acid sequence shown in FIG. 5. A potential N-myristoylation site exists between amino acids 24 and 29 of the amino acid sequence shown in FIG. 5. Potential casein kinase IT phosphorylation sites exist between amino acids 123–126, 185–188, 200–203, 252–255, 257–260, 271–274, and 283–286 of the amino acid sequence shown in FIG. 5. A potential transmembrane domain exists between amino acids 137 to 158 of the sequence shown in FIG. 5. It is presently believed that the polypeptide does not include a signal sequence.

Analysis of the amino acid sequence of the full-length DNA98853 polypeptide suggests that portions of it possess homology to members of the tumor necrosis factor receptor family, thereby indicating that DNA98853 polypeptide may be a novel member of the tumor necrosis factor receptor family. There are three apparent extracellular cysteine-rich domains characteristic of the TNFR family [see, Naismith and Sprang, *Trends Biochem. Sci.*, 23:74–79 (1998)], of which the first two CRDs have 6 cysteines while the third CRD has 4 cysteines.

Conclusion

The results of these experiments demonstrated that the present FLIP method has a high success rate in efficiently cloning a wide variety of genes.

REFERENCES

The practice of the present invention will employ, unless otherwise indicated, conventional techniques of PCR, molecular biology and the like, which are within the skill of the art. Such techniques are explained fully in the literature. See e.g., Molecular Cloning: A Laboratory Manual, (J. Sambrook et al., Cold Spring Harbor Laboratory, Cold Spring Harbor, N.Y., 1989); Current Protocols in Molecular Biology (F. Ausubel et al. eds., 1987 and updated); Essential Molecular Biology (T. Brown ed., IRL Press 1991); Gene Expression Technology (Goeddel ed., Academic Press 1991); Methods for Cloning and Analysis of Eukaryotic Genes (A. Bothwell et al. eds., Bartlett Publ. 1990); Gene Transfer and Expression (M. Kriegler, Stockton Press 1990); Recombinant DNA Methodology II (R. Wu ed., Academic Press 1995); PCR: A Practical Approach (M. McPherson et al., IRL Press at Oxford University Press 1991); *Oligonucleotide Synthesis* (M. Gait ed., 1984); Cell Culture for Biochemists (R. Adams ed., Elsevier Science Publishers 1990); Gene Transfer Vectors for Mammalian Cells (J. Miller & M. Calos eds., 1987).

What is claimed is:

1. A method of amplifying and isolating a nucleic acid molecule of interest from a mixture of nucleic acid molecules, comprising:
   (i) providing a recombinant nucleic acid library with a heterogeneous population of methylated, circular nucleic acid molecules as template molecules;
   (ii) annealing a first and a second primer to complementary strands of the circular nucleic acid molecule, to produce an annealed mixture, wherein
   the two primers extend in opposite directions relative to each other during polymerase chain reaction;
   the 5' ends of the two primers are adjacent to each other; and
   wherein each primer is identical in sequence to its corresponding sequence in the nucleic acid molecule of interest;
   (iii) subjecting the annealed mixture to polymerase chain reaction, thereby producing an amplified mixture containing linear amplicons;
   (iv) digesting the amplified mixture with an enzyme that selectively cleaves methylated nucleic acid, thereby eliminating the template molecules and enriching the nucleic acid molecule of interest; and
   (v) isolating the nucleic acid molecule of interest.

2. The method of claim 1, wherein the two primers are phosphorylated on their 5' ends.

3. The method of claim 2, further comprising ligating the linear amplicons prior to the digesting step to produce circular replicons.

4. The method of claim 2, wherein the template molecules comprise a cloning vector and the method further comprises, after the digesting step, isolating amplicons larger than the size of the cloning vector, and ligating the isolated larger amplicons.

5. The method of claim 4, wherein the larger amplicons are isolated by gel purification.

6. The method of claim 1, wherein the enzyme is a restriction endonuclease.

7. The method of claim 6, wherein the restriction endonuclease is Dpn I.

8. The method of claim 1, wherein multiple recombinant nucleic acid libraries are provided in a single mix for polymerase chain reaction.

9. The method of claim 1, wherein the nucleic acid library is a double-stranded DNA library wherein the DNA is methylated.

10. The method of claim 1, wherein the nucleic acid library is a human cDNA library.

11. The method of claim 1, wherein the recombinant DNA library is a human genomic DNA library.

12. The method of claim 1, wherein the nucleic acid molecule of interest is represented in the library at a frequency of equal to or less than one in $5 \times 10^5$ clones.

13. The method of claim 1, wherein the nucleic acid molecule of interest is represented in the library at a frequency of equal to or less than one in $1 \times 10^6$ clones.

14. The method of claim 3, further comprising transforming the circular replicons into a suitable host cell after the digesting step, to generate clones.

15. The method of claim 14, wherein the host cell is a competent bacterial host cell.

16. The method of claim 14, further comprising screening the clones to identify the clone containing the nucleic acid molecule of interest.

17. The method of claim 14, further comprising sequencing the nucleic acid isolated from the clones.

18. The method of claim 8, wherein a solution of the single mix is applied to wells of a 96-well microtiter plate and the polymerase chain reaction is performed on the microtiter plate to isolate multiple nucleic acid molecules of interest simultaneously.

19. A method of amplifying and isolating a nucleic acid molecule of interest from a recombinant nucleic acid library, comprising:
   (i) providing a recombinant nucleic acid library with a heterogeneous population of methylated, circular nucleic acid molecules as template molecules;
   (ii) annealing a first and a second primer to complementary strands of the circular nucleic acid molecule, to produce an annealed mixture, wherein
   the two primers extend in opposite directions relative to each other during polymerase chain reaction;
   the 5' ends of the two primers are adjacent to each other; and
   wherein each primer is identical in sequence to its corresponding sequence in the nucleic acid molecule of interest;
   (iii) subjecting the annealed mixture to polymerase chain reaction, thereby producing an amplified mixture containing amplicons;
   (iv) ligating the amplicons in a ligation mix to produce circular replicons;
   (v) digesting the ligation mix with an enzyme that selectively cleaves methylated nucleic acid, thereby eliminating the template molecules and enriching the nucleic acid molecule of interest;

(vi) transforming the replicons into a suitable host cell to generate transformed clones; and (vii) isolating the nucleic acid molecule of interest.

20. The method of claim 19, further comprising screening the transformed clones to identify the clone containing the nucleic acid molecule of interest.

21. The method of claim 19, wherein greater than 50 cDNA libraries are provided in a single mix for polymerase chain reaction.

22. The method of claim 9, wherein multiple double-stranded DNA libraries are provided in a single mix for polymerase chain reaction.

* * * * *

UNITED STATES PATENT AND TRADEMARK OFFICE
CERTIFICATE OF CORRECTION

PATENT NO. : 6,607,899 B2 Page 1 of 1
APPLICATION NO. : 10/119466
DATED : August 19, 2003
INVENTOR(S) : Clarissa J. Chui et al.

It is certified that error appears in the above-identified patent and that said Letters Patent is hereby corrected as shown below:

Title Page, item [73], insert above (21) --Assignee: Genentech, Inc., South San Francisco, CA (US)--

Title Page, item [74], in column 2, below "Assistant Examiner-Juliet C. Einsmann" insert therefor --Attorney, Agent or Firm - Paul Naik and Lee K. Tan--

Signed and Sealed this

Twenty-ninth Day of January, 2008

JON W. DUDAS
*Director of the United States Patent and Trademark Office*

UNITED STATES PATENT AND TRADEMARK OFFICE
CERTIFICATE OF CORRECTION

PATENT NO. : 6,607,899 B2  
APPLICATION NO. : 10/119466  
DATED : August 19, 2003  
INVENTOR(S) : Clarissa J. Chui et al.

Page 1 of 1

It is certified that error appears in the above-identified patent and that said Letters Patent is hereby corrected as shown below:

On the Title page, item [73] insert --Assignee: Genentech, Inc. , South San Francisco, CA (US)--

On the Title page, in column 2, below "Assistant Examiner-Juliet C. Einsmann" insert therefor --Attorney, Agent or Firm - Paul Naik and Lee K. Tan--

Signed and Sealed this

Fifth Day of February, 2008

JON W. DUDAS  
*Director of the United States Patent and Trademark Office*